(12) United States Patent
Takakura et al.

(10) Patent No.: US 8,518,665 B2
(45) Date of Patent: Aug. 27, 2013

(54) METHODS FOR MAKING 3-INDOLE-PYRUVIC ACID FROM TRYPTOPHAN USING A TRYPTOPHAN DEAMINASE

(71) Applicants: Yasuaki Takakura, Kanagawa (JP); Seiichi Hara, Kanagawa (JP); Toshiki Taba, Kanagawa (JP); Shunichi Suzuki, Kanagawa (JP); Masakazu Sugiyama, Kanagawa (JP); Kunihiko Watanabe, Kanagawa (JP); Kenzo Yokozeki, Kanagawa (JP)

(72) Inventors: Yasuaki Takakura, Kanagawa (JP); Seiichi Hara, Kanagawa (JP); Toshiki Taba, Kanagawa (JP); Shunichi Suzuki, Kanagawa (JP); Masakazu Sugiyama, Kanagawa (JP); Kunihiko Watanabe, Kanagawa (JP); Kenzo Yokozeki, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/684,888

(22) Filed: Nov. 26, 2012

(65) Prior Publication Data

US 2013/0084610 A1   Apr. 4, 2013

Related U.S. Application Data

(60) Division of application No. 12/711,719, filed on Feb. 24, 2010, now Pat. No. 8,394,940, which is a continuation of application No. PCT/JP2008/064635, filed on Aug. 15, 2008.

(30) Foreign Application Priority Data

Aug. 24, 2007 (JP) .................................. 2007-218955

(51) Int. Cl.
*C12P 1/00* (2006.01)
*C12P 21/06* (2006.01)

(52) U.S. Cl.
USPC ........................................... 435/41; 435/68.1

(58) Field of Classification Search
None
See application file for complete search history.

(56) References Cited

U.S. PATENT DOCUMENTS

| 4,551,471 | A | 11/1985 | De Luca et al. |
|---|---|---|---|
| 5,002,963 | A | 3/1991 | De Luca et al. |
| 6,605,709 | B1 | 8/2003 | Breton |
| 2005/0009153 | A1 | 1/2005 | Sugiyama et al. |
| 2005/0153405 | A1 | 7/2005 | Sugiyama et al. |
| 2005/0282260 | A1 | 12/2005 | Hicks et al. |

FOREIGN PATENT DOCUMENTS

| EP | 0 421 946 A2 | 4/1991 |
|---|---|---|
| JP | 57-146573 A | 9/1982 |
| JP | 59-95894 | 6/1984 |
| JP | 62-501912 A | 7/1987 |
| JP | 04-218386 A | 8/1992 |
| WO | WO 87/00169 | 1/1987 |
| WO | WO 03/056026 A1 | 7/2003 |
| WO | WO 03/091396 A2 | 11/2003 |

OTHER PUBLICATIONS

G. Massad, et al., "*Proteus mirabilis* Amino Acid Deaminase: Cloning, Nucleotide Sequence, and Characterization of *aad*", Journal of Bacteriology, vol. 177, No. 20, Oct. 1995, p. 5878-5883.
E. Takahashi, et al., "Cloning of L-Amino Acid Deaminase Gene from *Proteus vulgaris*", Biosci. Biotechnol. Biochem., 63 (12), 2244-2247, 1999.
J. A. Duerre, et al. "L-Amino Acid Oxidases of *Proteus rettgeri*", Journal of Bacteriology, vol. 121, No. 2, Feb. 1975. p. 656-663.
Galye et ai, Identification of regions in interleukin-1 alpha important for activity. J Bioi Chem. Oct. 15, 1993;268(29):22105-11.
Whisstock et ai, Prediction of protein function from protein sequence and structure. Q Rev Biophys. Aug. 2003;36(3):307-40 Review.
UniProt database Acc# B2PWP6 PROST Jul. 1, 2008. Alignment with SEQ ID No. 2.
UniProt database Acc# B6XDVO_9ENTR Jan. 20, 2009. Alignment with SEQ ID No. 2.

*Primary Examiner* — Sheridan Swope
(74) *Attorney, Agent, or Firm* — Oblon, Spivak, McClelland, Maier & Neustadt, L.L.P.

(57) ABSTRACT

It is an object of the present invention to provide a procedure for realizing inexpensive and simple production of 3-indole-pyruvic acid. A transformant is made using a polynucleotide having a specific nucleotide sequence encoding a protein having an oxidase activity, and oxidase is generated by culturing the transformant in a medium to accumulate the oxidase in the medium and/or the transformant. Further, tryptophan is converted into 3-indole-pyruvic acid in the presence of the transformant and/or a culture thereof to produce 3-indole-pyruvic acid.

13 Claims, No Drawings

METHODS FOR MAKING 3-INDOLE-PYRUVIC ACID FROM TRYPTOPHAN USING A TRYPTOPHAN DEAMINASE

CROSS-REFERENCE TO RELATED APPLICATIONS

The present application is a division of U.S. Ser. No. 12/711,719, filed Feb. 24, 2010, which is a continuation of International patent application PCT/JP2008/064635, filed on Aug. 15, 2008, which claims priority to Japanese patent application JP 2007-218955, filed on Aug. 24, 2007.

TECHNICAL FIELD

The present invention relates to a novel oxidase gene and a novel method for producing 3-indole-pyruvic acid utilizing the gene.

BACKGROUND ART

In a chemical method for producing 3-indole-pyruvic acid disclosed by Giovanna De Luca et al., 3-indole-pyruvic acid was produced with a yield of 50 to 62% by reacting tryptophan as a starting material with pyridine aldehyde in the presence of a base for dehydrating a proton acceptor (see JP Sho-62-501912 [Patent Document 1], International Publication 87/00169 Pamphlet [Patent Document 2]). In this method, the required base and pyridine aldehyde are expensive and the yield is low. As a result, production cost are very high. Politi Vincenzo et al. produced 3-indole-pyruvic acid with the yield of 64% by a condensation reaction using indole and ethyl-3-bromopyruvate ester oxime as raw materials followed by acid hydrolysis (see Europe Patent Application Publication No. 421946 [Patent Document 3]). This method, however, requires a purification step using silica gel, the yield is low, the raw materials are expensive and the industrial production cost is very high.

On the other hand, an enzymatic method for production of 3-indole-pyruvic acid using an aminotransferase is known (see the following reaction formula 1).

In an example of this method, 3-indole-pyruvic acid is generated from 40 mM L-tryptophan (L-Trp) and 80 mM 2-ketoglutaric acid by reacting L-Trp and 2-ketoglutaric acid with an L-tryptophan aminotransferase derived from *Candida maltosa* and purifying the resulting 3-indole-pyruvic acid using an ion exchange resin to achieve the yield of 72% (see Bobe Ruediger et al., East Germany Patent DD 297190 [Patent Document 4]). By reacting L-Trp and 2-ketoglutaric acid with an aspartate aminotransferase to generate 3-indole-pyruvic acid, which is then purified by extracting the reaction solution with petroleum ether and fractionating by column chromatography and the fraction is collected (see Mario Materazzi et al., JP Sho-59-95894-A [Patent Document 5]). Aminotransferases encoded by an aspC gene and a tyrB gene derived from *Escherichia coli* is described in International Publication No. 2003/091396 Pamphlet [Patent Document 6] and US Patent Application Publication No. 2005/0282260 [Patent Document 7]. In these methods of using an aminotransferase, the yield is low and a keto acid (e.g. 2-ketoglutaric acid) is required as an amino group acceptor in addition to L-Trp. In addition, an amino acid corresponding to the amino group acceptor present in an amount of equivalent moles to 3-indole-pyruvic acid to be generated is produced as a byproduct. Furthermore, an excessive amount of keto acid relative to L-Trp is added to the reaction system in order to enhance the yield. Thus, unreacted keto acid remains after the reaction. Due to these reasons, a purification step employing an ion exchange resin is required in order to collect the 3-indole-pyruvic acid from the reaction solution. Thus, manipulation of the reaction is complicated and the cost is high.

Another known method for producing 3-indole-pyruvic acid from L-Trp employs an L-amino acid oxidase a. In this regard, however, 3-indole-pyruvic acid is decomposed into indoleacetic acid (see the following reaction formula 3) by hydrogen peroxide which is produced as a byproduct when tryptophan is oxidized by L-amino acid oxidase (see the following reaction formula 2). Thus, a method of decomposing hydrogen peroxide by adding catalase to the reaction system (see the following reaction formula 4) is proposed (see U.S. Pat. No. 5,002,963 to De Luca, et al., 1991 [Patent Document 8]).

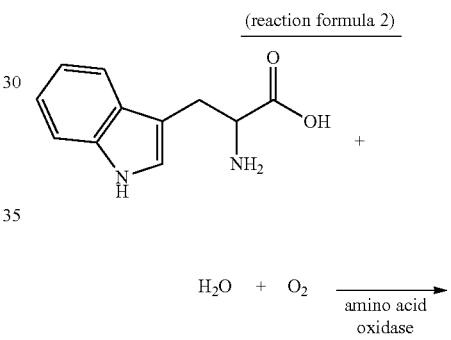

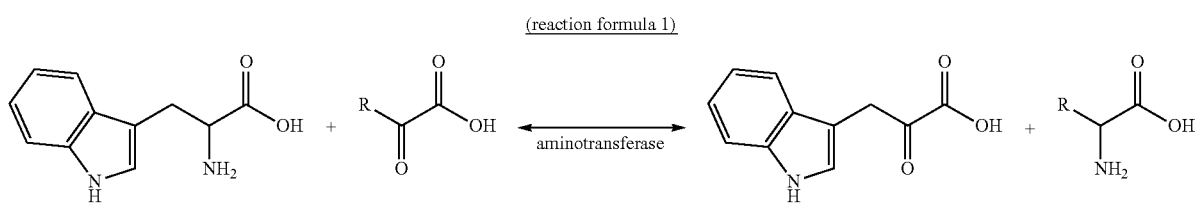

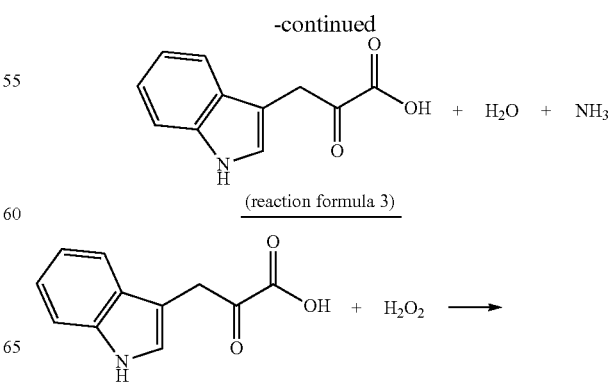

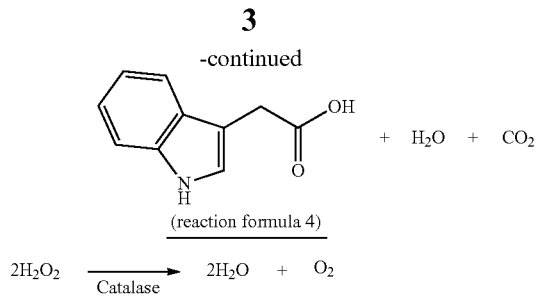

(reaction formula 4)

$$2H_2O_2 \xrightarrow{\text{Catalase}} 2H_2O + O_2$$

In the above method, an immobilized enzyme column is used in which L-amino acid oxidase derived from a snake venom and catalase derived from bovine liver have been immobilized to a carrier. Then, a solution containing L-Trp is passed through the column to react, and the produced 3-indole-pyruvic acid is adsorbed to an ion exchange column, eluted with methanol, subsequently exsiccated and collected. However, in this method, only 0.2 g of 3-indole-pyruvic acid is acquired from 0.5 g of L-Trp, and the yield is low (40%). Further, in this method, the steps such as immobilizing the enzymes and purifying by the ion exchange resin are complicated and it is also necessary to collect or recycle unreacted L-Trp, which leads to an increased cost.

The L-amino acid oxidase derived from microorganisms is provided by John A. Duerre et al., who crudely purified L-amino acid oxidase (deaminase) derived from *Proteus rettgeri* and detected an oxidation activity for L-Trp by an activity measurement method of detecting an amount of consumed oxygen (see Journal of Bacteriology, 1975, vol. 121, No. 2, p656-663 [Nonpatent Document 1]). Furuyama et al. confirmed that L-phenylalanine oxidase derived from *Pseudomonas* sp.P-501 also acted upon L-Trp by an activity measurement method by detecting the amount of consumed oxygen (see Noda Institute for Scientific Research, JP Sho-57-146573-A [Patent Document 9]).

However, in any of these methods, the oxidase activity was detected by measuring the amount of consumed tryptophan, the amount of consumed oxygen or the amount of produced hydrogen peroxide. The indole-pyruvic acid was not directly quantified. This seems to be because 3-indole-pyruvic acid is decomposed into indoleacetic acid by hydrogen peroxide produced by the reaction with amino acid oxidase. On the other hand, there is no example in which 3-indole-pyruvic acid is generated using a microbial cell or a treated microbial cell. Further, how tryptophan is metabolized by the microorganism and what metabolite is generated by the microorganism are unknown.

The microorganisms having oxidase activity and belonging to genera *Achromobacter, Proteus, Morganella, Pseudomonas* and *Neurospora* are disclosed in International Publication No. 03/056026 Pamphlet (patent Document 10). However, when 3-indole-pyruvic acid was industrially produced on a large scale, there was a limit to produce it by a microbial cell reaction alone.

Further, in the method of using aminotransferase or the method of using L-amino acid oxidase derived from the snake venom among the aforementioned technology known publicly, the reaction yield is low, keto acid as the byproduct or unreacted L-tryptophan remains and is mixed in the reaction solution. Thus, a chromatographic separation step is required to collect the 3-indole-pyruvic acid, thus the manipulation is complicated and the cost is high.

Under the circumstance as above, it is required to develop the method for producing 3-indole-pyruvic acid inexpensively and conveniently.

Patent Document 1: JP Sho-62-501912-A
Patent Document 2: International Publication WO87/00169 Pamphlet
Patent Document 3: Europe Patent Application Publication No. 421946
Patent Document 4: East Germany Patent DD 297190
Patent Document 5: JP Sho-59-95894-A
Patent Document 6: International Publication No. WO2003/091396 Pamphlet
Patent Document 7: US Patent Application Publication No. 2005/0282260
Patent Document 8: U.S. Pat. No. 5,002,963
Patent Document 9: JP Sho-57-146573-A
Patent Document 10: International Publication No. 03/056026 Pamphlet
Nonpatent Document 1: Journal of Bacteriology, 1975, vol. 121, No. 2, p656-663.

DISCLOSURE OF INVENTION

Problem to be Solved by the Invention

3-Indole-pyruvic acid is extremely useful as a synthetic intermediate of various pharmaceuticals and drinks and foods, particularly sweeteners. It is an object of the present invention to provide an inexpensive and simple procedure for realizing the production of 3-indole-pyruvic acid.

Means for Solving Problem

As a result of an extensive study in the light of the above circumstance, the present inventors found that 3-indole-pyruvic acid is generated and can be collected by cloning a novel oxidase gene from a microorganism having an oxidase activity to construct a transformant and reacting tryptophan in the presence of the transformant. Preferably, reactivity is further enhanced by constructing the transformant as a microbial strain which highly expresses the gene. The present inventors further have found that 3-indole-pyruvic acid with a higher yield is obtained by reacting tryptophan in the presence of a culture obtained by subjecting the transformant to a high density cultivation or a treated culture, and completed the present invention.

Accordingly, the present invention provides the respective inventions as follows.

[1] A polynucleotide selected from a group consisting of the following (a) to (e):
(a) a polynucleotide encoding a protein comprising the amino acid sequence of SEQ ID NO:2;
(b) a polynucleotide encoding a protein which consists of an amino acid sequence comprising a substitution, deletion and/or insertion of one or several amino acids in the amino acid sequence of SEQ ID NO:2 and has an oxidase activity;
(c) a polynucleotide encoding a protein which consists of an amino acid sequence having 90% or more homology to the amino acid sequence of SEQ ID NO:2 and has an oxidase activity;
(d) a polynucleotide comprising the nucleotide sequence of nucleotide positions 61 to 1476 in the nucleotide sequence of SEQ ID NO:1; and
(e) a polynucleotide which hybridizes with a nucleotide sequence complementary to the nucleotide sequence of the nucleotide positions 61 to 1476 in the nucleotide sequence of SEQ ID NO:1 or with a probe capable of being prepared from said sequence under a stringent condition, and encodes a protein having an oxidase activity.

[2] The polynucleotide according to the above described [1], wherein said stringent condition is a condition where washing is performed at a salt concentration corresponding to 1×SSC and 0.1% SDS at 60° C.

[3] A recombinant polynucleotide comprising the polynucleotide according to the above described [1] or [2].

[4] A transformant introduced with the recombinant polynucleotide according to the above described [3].

[5] A method for producing oxidase, comprising culturing the transformant according to the above described [4] in a medium to accumulate the oxidase in the medium and/or the transformant.

[6] A method for producing 3-indole-pyruvic acid, comprising converting tryptophan into 3-indole-pyruvic acid in the presence of the transformant according to the above described [4] and/or a culture thereof.

[7] The method for producing 3-indole-pyruvic acid according to the above described [6], wherein superoxide dismutase is added to a reaction system which converts tryptophan into 3-indole-pyruvic acid.

[8] The method for producing 3-indole-pyruvic acid according to the above described [6], wherein a transformant which expresses superoxide dismutase and/or a culture thereof is added to a reaction system which converts tryptophan into 3-indole-pyruvic acid.

[9] The method for producing 3-indole-pyruvic acid according to the above described [8], wherein said culture is obtained by rupturing cell membrane of the transformant which expresses said superoxide dismutase.

Unless otherwise indicated herein, a sequence number indicates the sequence number described in Sequence Listing.

Effect of the Invention

According to the present invention, the polynucleotide encoding the protein having the oxidase activity is provided. When such a polynucleotide is utilized, it is possible to produce 3-indole-pyruviic acid, which is the raw material of monatin (a sweetener) or the like can be produced conveniently with the high yield by utilizing tryptophan, and it is industrially useful particularly in the field of foods.

BEST MODES FOR CARRYING OUT THE INVENTION

1. Polynucleotide According to the Present Invention

First, the present invention provides a polynucleotide encoding a protein having an oxidase activity.

In the present invention, oxidase means an enzyme that catalyzes an oxidative deamination of a substrate such as an amino acid. Having the oxidase activity means having an enzymatic activity of such oxidase. As a representative oxidase catalyzed reaction, a reaction of converting tryptophan into 3-indole-pyruvic acid (e.g., the reaction shown in the following reaction formula 5 may be included) can be shown. The amino acid such as tryptophan includes any of an L-form and a D-form, and D- and L-forms, but ordinarily indicates the L-form.

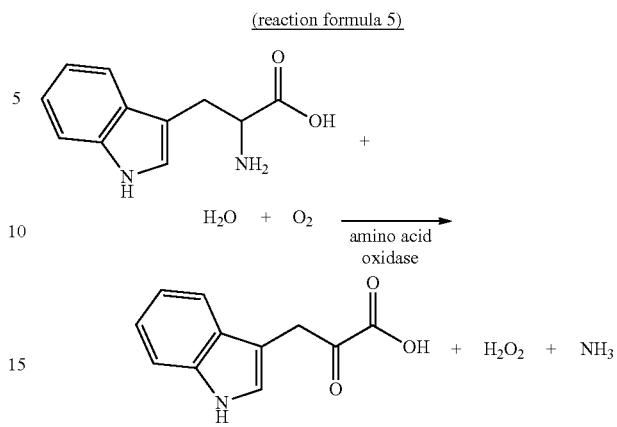

(reaction formula 5)

In the present invention, the oxidase preferably catalyzes the aforementioned reaction and has a catalase activity. The catalase activity is the activity that catalyzes a decomposition reaction of hydrogen peroxide, and for example, catalyzes the reaction shown in the following reaction formula 6.

(reaction formula 6)

The polynucleotide of the present invention encodes a protein having an oxidase activity, and may include (a) a polynucleotide encoding the protein having an amino acid sequence of SEQ ID NO:2.

The protein having the amino acid sequence of SEQ ID NO:2 was newly isolated from *Providencia rettgeri* AJ2770 strain and identified as the amino acid sequence of the protein having the oxidase activity by the present inventors. AJ2770 strain was internationally deposited to Ministry of International Trade and Industry, Agency of Industrial Science and Technology, National Institute of Bioscience and Human-Technology (currently Incorporated Administrative Agency, National Institute of Advanced Industrial Science and Technology) on Nov. 28, 1985, and deposit number FERM BP-941 was given thereto. AJ2770 strain was originally identified as *Proteus rettgeri*, but as a result of re-identification, it was classified into *Providencia rettgeri* (*Providencia rettgeri* sp).

A protein having the oxidase activity shown in the above reaction formula 5 can also be isolated from *Proteus rettgeri* IFO13501 strain. IFO13501 strain was deposited to Institute for Fermentation Osaka (17-85 Juso-honmachi 2-chome, Yodogawa-ku, Osaka, Japan), but its business has been transferred to NITE Biological Resource Center (NBRC) in Department of Biotechnology (DOB), National Institute of Technology and Evaluation (NITE) since Jun. 30, 2002, and the microorganisms are available from NERC with reference to the above IFO No.

The polynucleotide of the present invention includes polynucleotides encoding substantially the same protein as the protein having the amino acid sequence of SEQ ID NO:2. Specifically, the following polynucleotide (b) and polynucleotide (c) may be included:

(b) polynucleotide encoding a protein which has an amino acid sequence comprising a substitution, deletion and/or insertion of one or several amino acids in the amino acid sequence of SEQ ID NO:2 and has the oxidase activity; and (c) polynucleotide encoding a protein which has an amino acid sequence having 90% or more homology to the amino acid sequence of SEQ ID NO:2 and has the oxidase activity.

The "several amino acids" in the polynucleotide (b) vary depending on positions and types of amino acid residues in a three-dimensional structure of the protein, are in the range in which the three-dimensional structure and the activity of the protein with the amino acid residues are not significantly impaired, and specifically are preferably 2 to 140, more preferably 2 to 95, more preferably 2 to 50, more preferably 2 to 30 and still more preferably 2 to 10 amino acid residues. The sequence having mutations of one or several amino acids can have the homology of 70% or more, preferably 80% or more, more preferably 90% or more, still more preferably 95% or more and still more preferably 98% or more to the sequence having no mutation. The homology as used herein is a concept that represents a level of matching the sequences between two or more of the sequences. As one simple evaluation method of the homology, the number of the amino acid residues in a full length of the longer amino acid sequence in the two sequences is made a denominator, the number of the matched amino acid residues that mutually correspond in the two sequences to be compared is made a numerator, and this fraction can be calculated and multiplied by 100 to obtain the level expressed numerically. The homology can be calculated in great detail according to logic of bioinformatics, and various software have been developed for comparing similarity in the multiple sequences. Examples of the software for calculating the homology may include BLAST.

In the polynucleotide (c), the homology to the amino acid sequence of SEQ ID NO:2 is preferably 70% or more, more preferably 80% or more, more preferably 90% or more, more preferably 95% or more and still more preferably 98% or more.

The polynucleotide (b) or the polynucleotide (c) is necessary to have the oxidase activity. It is desirable that the enzyme encoded by the polynucleotide retains the enzymatic activity at about a half or more, more preferably 80% or more and still more preferably 90% or more of the protein having the amino acid sequence of SEQ ID NO:2 in a state having no mutation, particularly under a condition at 30° C. at pH 8. For example, it is desirable to retain the enzymatic activity at about a half or more, more preferably 80% or more and still more preferably 90% or more of the protein having the amino acid sequence of SEQ ID NO:2, under the condition at 30° C. at pH 8.

The mutation of the amino acid as shown in the polynucleotide (b) is obtained, for example, by previously designing an amino acid sequence modified so that an amino acid residue at a certain position in the amino acid sequence of SEQ ID NO:2 is substituted, deleted and/or inserted by site-specific mutagenesis, and expressing a nucleotide sequence corresponding to this amino acid sequence.

The mutation of the amino acid as shown in the polynucleotide (C) is also obtained, for example, by previously designing an amino acid sequence modified so that the amino acid sequence in the certain region of the amino acid sequence of SEQ ID NO:2 has the 90% or more homology to the amino acid sequence of SEQ ID NO:2 by the site-specific mutagenesis, and expressing a nucleotide sequence corresponding to this amino acid sequence.

The substitution, the deletion and/or the insertion of nucleotides as mentioned above includes naturally occurring mutations such as differences depending on species and strains of the microorganisms. Substantially the same protein as the protein having the amino acid sequence of SEQ ID NO:2 is obtained by expressing the polynucleotide encoding the amino acids having the mutation as mentioned above in an appropriate cell and examining the enzymatic activity of the expressed product.

Multiple nucleotide sequences defining each amino acid sequence can be present due to degeneracy of codons in the aforementioned polynucleotides (a) to (c). The representative of specific examples of the polynucleotides (a) to (c) may include the following polynucleotide (d):

(d) polynucleotide having a nucleotide sequence of nucleotide positions 61 to 1476 in a nucleotide sequence of SEQ ID NO:1.

The polynucleotide consisting of the nucleotide sequence of SEQ ID NO:1 has been isolated from *Providencia rettgeri* AJ2770 strain. The polynucleotide consisting of the nucleotide sequence of nucleotide positions 61 to 1476 in SEQ ID NO:1 is a region of a coding sequence (CDS), and the amino acid sequence encoded by this CDS region is shown in SEQ ID NO:2.

Various gene recombination techniques mentioned below can be carried out in accordance with descriptions in Molecular Cloning, 2nd edition, Cold Spring Harbor press (1989) or the other references.

The polynucleotide (d) of the present invention can be obtained from the microorganism having the oxidase activity, preferably the microorganism having the amino acid oxidase activity that acts upon tryptophan and the catalase activity. For example, it can be acquired from chromosomal DNA or DNA library of *Providencia rettgeri* by PCR (polymerase chain reaction, see White, T. J. et al; Trends Genet., 5, 185, 1989) or hybridization. Primers used for PCR can be designed based on an internal amino acid sequence determined based on the oxidase purified from *Providencia rettgeri*. The primers and a probe for the hybridization can be designed based on the nucleotide sequence of SEQ ID NO:1, and it can be isolated using the probe. When the primers having the sequences corresponding to 5'-untranslated region and 3'-untranslated region are used as the primers for PCR, the full length of the coding region of the enzyme can be amplified. Specifically, the 5' side primer may include the primer having the nucleotide sequence of an upstream region from the nucleotide number 61 in SEQ ID NO:1. The 3' side primer may include the primer having the sequence complementary to the nucleotide sequence of a downstream region from the nucleotide number 1476 in SEQ ID NO:1.

The primers can be synthesized, for example, using a DNA synthesizer model 380B supplied from Applied Biosystems and using a phosphoamidite method (see Tetrahedron Letters, 1981, 22, 1859) according to standard methods. PCR can be performed, for example, using Gene Amp PCR System 9600 (supplied from Perkin Elmer) and TaKaRa LA PCR in vitro Cloning Kit (supplied from Takara Shuzo Co., Ltd.) according to the methods designated by suppliers of respective manufacturers.

The polynucleotide of the present invention includes substantially the same polynucleotide as the polynucleotide (d). Substantially the same polynucleotide like this may include the following polynucleotide (e):

(e) polynucleotide which hybridizes with a nucleotide sequence complementary to the nucleotide sequence of the nucleotide positions 61 to 1476 in the nucleotide sequence of SEQ ID NO:1 or with a probe capable of being prepared from the sequence under a stringent condition, and encodes a protein having an oxidase activity.

The "stringent condition" in the present invention refers to the condition where a so-called specific hybrid is formed whereas non-specific hybrid is not formed. Although it is difficult to clearly quantify this condition, examples thereof may include the condition where a pair of polynucleotides having high homology, e.g., polynucleotides having the homology of 50% or more, more preferably 80% or more, still more preferably 90% or more, among others preferably 95% or more and still more preferably 97% or more are hybridized to each other whereas a pair of polynucleotides having lower homology than that are not hybridized to each other. Also mentioned is a washing condition of an ordinary Southern hybridization, i.e., hybridization at salt concentrations equivalent to 1×SSC and 0.1% SDS at 60° C. and preferably 0.1×SSC and 0.1% SDS at 60° C. The genes which hybridize under such a condition include those in which a stop codon exists in the internal sequence or an activity is lost by the mutation of an active center. However, those may be easily removed by ligating the gene to the commercially available vector, expressing it in the appropriate host, and measuring the enzymatic activity of the expressed product by the methods described later.

The probe in the polynucleotide (e) consists of the sequence capable of being prepared from the sequence complementary to the nucleotide sequence in SEQ ID NO:1. Such a probe can be made by PCR with a DNA fragment containing the nucleotide sequence of SEQ ID NO:1 as a template using oligonucleotides made based on the nucleotide sequence of SEQ ID NO:1 as the primers. When the DNA fragment having the length of about 300 bp is used as the probe, the washing condition in the hybridization may include washing with 2×SSC and 0.1% SDS at 50° C.

The aforementioned polynucleotide (e) is necessary to have the oxidase activity. For example, it is desirable that the enzyme encoded by the polynucleotide (e) retains the enzymatic activity at about a half or more, more preferably 80% or more and still more preferably 90% or more of the protein defined by the amino acid sequence encoded by the aforementioned polynucleotide (d), under the condition at 30° C. at pH 8. Specifically, it is desirable to retain the enzymatic activity at about a half or more, more preferably 80% or more and still more preferably 90% or more of the protein encoded by the nucleotide sequence of the nucleotide numbers 61 to 1476 in the nucleotide sequence of SEQ ID NO:1, under the condition at 30° C. at pH 8.

A way for obtaining the polynucleotide (e) is not particularly limited, and for example, the polynucleotide (e) can be obtained by isolating the polynucleotide which hybridizes with the polynucleotide consisting of the nucleotide sequence complementary to CDS of SEQ ID NO:1 or with the probe prepared from the same nucleotide sequence under the stringent condition, and encodes the protein having the oxidase activity, from the polynucleotides encoding the enzyme having the mutation or the cell having the polynucleotides.

The probe can be made based on the nucleotide sequence of SEQ ID NO:1 according to a standard method. The method of isolating the objective polynucleotide by picking up the polynucleotide which is hybridized with a used probe may be performed according to a standard method. For example, a DNA probe can be prepared by amplifying the nucleotide sequence cloned into a plasmid or a phage vector, cutting out the nucleotide sequence to be used as the probe with restriction enzymes and extracting it. Sites to be cut out can be controlled depending on the objective polynucleotide.

The polynucleotide modified in this manner can be acquired by conventionally known mutagenesis. Examples of the mutagenesis may include the method of treating the polynucleotide encoding the enzyme, e.g., the above polynucleotide (d) with hydroxylamine or the like in vitro, and method of treating bacteria having the polynucleotide encoding the enzyme and belonging to genus *Escherichia* with ultraviolet light or a mutagen such as N-methyl-N'-nitro-N-nitrosoguanidine (NTG) or nitrous acid ordinary used for the artificial mutagenesis.

2. Recombinant Polynucleotide and Transformant, and Method for Producing Oxidase According to the Present Invention Second, the present invention provides a recombinant polynucleotide having the aforementioned polynucleotide of the present invention, a transformant introduced with the recombinant polynucleotide, and a method for producing oxidase, which is characterized by culturing the transformant in a medium to accumulate the oxidase in the medium and/or the transformant.

As a host for expressing the protein specified by the polynucleotide, various prokaryotic cells including the genus *Escherichia* such as *Escherichia coli* and *Bacillus subtilis*, and various eukaryotic cells including *Saccharomyces cerevisiae*, *Pichia stipitis* and *Aspergillus oryzae* can be used.

The recombinant polynucleotide used for introducing the polynucleotide into the host can be prepared by inserting the polynucleotide to be introduced into the vector corresponding to the type of the host in a form in which the protein encoded by the polynucleotide can be expressed. As a promoter for expressing the polynucleotide of the present invention, if a promoter inherent in the oxidase gene in *Providencia rettgeri* works in the host cell, the promoter can be used. If necessary, the other promoter may be ligated to the polynucleotide of the present invention to express the polynucleotide under the control of this promoter.

The method of transformation for introducing the recombinant polynucleotide into the host cell may include D. M. Morrison's method (Methods in Enzymology 68, 326, 1979) or the method of enhancing permeability of the polynucleotide by treating receiving microbial cells with calcium chloride (Mandel, M. and Higa, A., J. Mol. Biol., 53, 159, 1970).

In the case of producing a protein on a large scale using the recombinant polynucleotide technology, a preferable embodiment may include formation of an inclusion body of the protein, which is treated to associate the protein in the transformant producing the protein. The advantages of this expression production method may include the protection of the objective protein from digestion by proteases present in the microbial cells, and ready purification of the objective protein that may be performed by disruption of the microbial cells and the following centrifugation.

The protein inclusion body obtained in this manner is solubilized by a protein denaturing agent, which is then subjected to activation regeneration mainly by eliminating the denaturing agent, to be converted into the correctly refolded and physiologically active protein. There are many examples of such procedures, such as activity regeneration of human interleukin 2 (JP 61-257931 A).

To obtain the active protein from the protein inclusion body, a series of the manipulations such as solubilization and activity regeneration is required, and thus the manipulations is more complicate than those in the case of directly producing the active protein. However, when a protein which affects microbial cell growth is produced on a large scale in the microbial cells, the affection can be avoided by accumulating the protein as the inactive inclusion body in the microbial cells.

The methods for producing the objective protein on a large scale as the inclusion body may include methods of expressing the protein alone under control of a strong promoter, and methods of expressing the objective protein as a fusion protein with a protein known to be expressed in a large amount.

The method for making transformed *Escherichia coli* (*E. coli*) and producing the oxidase using this will be described more specifically below. When oxidase is produced in the microorganism such as *E. coli*, a polynucleotide encoding a precursor protein containing a leader sequence may be incorporated or a polynucleotide encoding a mature protein containing no leader sequence may be incorporated as the coding sequence of the protein. This can be appropriately selected depending on a production condition, a form and a use condition of the enzyme to be produced.

As the promoter for expressing the polynucleotide encoding the oxidase, the promoter ordinary used for producing a xenogenic protein in *E. coli* can be used, and examples thereof may include strong promoters such as T7 promoter, lac promoter, trp promoter, trc promoter, tac promoter, and PR promoter and PL promoter of lambda phage. As the vector, pUC19, pUC18, pBR322, pHSG299, pHSG298, pHSG399, pHSG398, RSF1010, pMW119, pMW118, pMW219 and pMW218 can be used. In addition, the vectors for phage polynucleotides can also be utilized. Further an expression vector that contains the promoter and can express the inserted polynucleotide sequence can also be used.

In order to produce the oxidase as a fusion protein inclusion body, a fusion protein inclusion body may be achieved by ligating a gene encoding other protein, preferably a hydrophilic peptide to an upstream or downstream of the oxidase gene. Such a gene encoding the other protein may be the one which increases an accumulation amount of the fusion protein and enhances solubility of the fusion protein after steps of denaturing and regenerating, and example of the candidates may include T7 gene 10, β-galactosidase gene, dehydrofolate reductase gene, interferon γ gene, interleukin-2 gene and prochymosin gene.

The ligation of these gene to the gene encoding the oxidase is performed so that reading frames of codons are matched. Such a ligation may be performed by ligation at an appropriate restriction enzyme site, or by utilization of synthetic polynucleotide with appropriate sequence.

In order to augment a production amount, it is sometimes preferable to ligate a terminator, i.e., a transcription termination sequence to the downstream of the fusion protein gene. This terminator may include rrnB terminator, T7 terminator, fd phage terminator, T4 terminator, terminator of tetracycline resistant gene, terminator of *Escherichia coli* trpA gene, and the like.

As a vector to introduce the gene encoding the oxidase or the fusion protein of the oxidase and the other protein into *E. coli*, so-called multiple copying types are preferable, and includes plasmids having a replication origin derived from ColE1, such as pUC type plasmids, pBR322 type plasmids or derivatives thereof. The "derivative" as used herein means the plasmids modified by the substitution, deletion and/or insertion of a nucleotide. The modification as used herein includes mutagenesis with the mutagen and UV irradiation, and modification such as the natural mutagenesis.

It is preferred that the vector has a marker such as an ampicillin resistant gene for selecting the transformant. As such a plasmid, expression vectors carrying strong promoters are commercially available [pUC types (supplied from Takara Shuzo Co., Ltd.), pPROK types (supplied from Clontech), pKK233-2 (supplied from Clontech) and the like].

The recombinant polynucleotide is obtained by ligating a polynucleotide fragment obtained by ligating the promoter, the gene encoding the oxidase or the fusion protein of the oxidase and the other protein and the terminator in some cases in this order, to a vector polynucleotide.

When *E. coli* cells are transformed using the recombinant polynucleotide and cultured, the oxidase or the fusion protein of the oxidase and the other protein is expressed and produced. As the host to be transformed, the strain usually used for the expression of a xenogenic gene can be used, and *Escherichia coli* JM109 strain is preferable. The methods of transforming and selecting the transformant are described in Molecular Cloning, 2nd edition, Cold Spring Harbor press (1989) or the other references.

When the fusion protein is expressed, the fusion protein may be composed so as to be able to cleave the oxidase therefrom using a restriction protease which recognizes a sequence such as the sequence of blood coagulation factor Xa or kallikrein, which is not present in the oxidase.

As the production media, the media usually used for culturing *E. coli*, such as M9-casamino acid medium and LB medium may be used. Culture conditions and production induction conditions may be appropriately selected depending on types of the vector marker, the promoter, the host bacterium and the like.

The oxidase or the fusion protein of the oxidase and the other protein may be recovered by the following method: when the oxidase or the fusion protein of the oxidase is solubilized in the microbial cells, the microbial cells may be collected and then disrupted or lysed, to obtain a crude enzyme solution. If necessary, the oxidase or the fusion protein thereof can further be subjected to purification in accordance with ordinary methods such as precipitation, filtration and column chromatography. In this case, methods utilizing an antibody against the oxidase or the fusion protein can also be utilized.

Where the protein inclusion body is formed, this may be solubilized with a denaturing agent. The inclusion body may be solubilized together with the microbial cells. However, considering the following purification process, it is preferable to remove the inclusion body before solubilization and then solubilize the inclusion body. recovering the inclusion body from the microbial cells may be performed in accordance with conventionally and publicly known methods. For example, the microbial cells are broken, and the inclusion body is recovered by centrifugation and the like. The denaturing agent that solubilizes the protein inclusion body may include guanidine-hydrochloric acid (e.g., 6 M, pH 5 to 8), urea (e.g., 8 M), and the like.

As a result of removal of the denaturing agent by dialysis and the like, the protein is regenerated as having the activity. Dialysis solutions used for the dialysis may include Tris-hydrochloric acid buffer, phosphate buffer and the like. The concentration may be 20 mM to 0.5 M, and pH may be 5 to 8.

It is preferred that the protein concentration utilized at a regeneration step is kept at about 500 µg/ml or less. In order to inhibit self-crosslinking of the regenerated oxidase, it is preferred that dialysis temperature is kept at 5° C. or below. Methods for removing the denaturing agent may include a dilution method and an ultrafiltration method in addition to this dialysis method. The regeneration of the activity can be expected by using any of these methods.

3. Method for Producing 3-Indole-Pyruvic Acid According to the Present Invention A method for producing 3-indole-pyruvic acid according to the present invention is characterized by having a step of converting tryptophan into 3-indole-pyruvic acid in the presence of the transformant of the present invention and/or the culture thereof. According to the production method of the present invention, the oxidase can be produced conveniently in a large amount. Thus, 3-indole-pyruvic acid can also be produced rapidly in the large amount.

Tryptophan used in the present invention may be any of an L-form and a D-form, and D- and L-forms, but it is desirable to employ the L-form in terms of easy availability and price.

The transformant of the present invention is as already described above. The culture of the transformant means ones obtained by culturing the transformant. Cultivation may be either a liquid cultivation or a solid cultivation, and the type of the medium is not particularly limited. Examples of the culture of the transformant may include the medium used for the cultivation, substances produced by the cultured transformant and mixtures thereof. These cultures may be treated for the purpose of retrieving the enzyme, e.g., treated with sonication, glass beads, French press, lyophilization, a lytic enzyme, an organic solvent or a surfactant. These treated cultures may be purified by the standard method such as liquid chromatography and ammonium sulfate fractionation, and additionally may be included in a carrageenan gel or a polyacrylamide gel or immobilized on a membrane of polyether sulfone or regenerated cellulose.

An amount of the transformant or the culture thereof may be the amount (effective amount) that elicits an objective effect, and those skilled in the art easily determine this effective amount by a simple preliminary experiment. For example, in the case of washed wet microbial cells, the effective amount can be 1 to 40 mg per 100 mL of the reaction solution.

In the production method of the present invention, when the aforementioned culture of the transformant of the present invention is allowed to act upon tryptophan, the culture of the transformant can be brought into contact with tryptophan. For example, the production method may include the method in which the transformant of the present invention is cultured in the medium to accumulate the oxidase in the transformant and/or the medium and tryptophan is added to this medium, and the method in which tryptophan is added to the culture of the transformant previously cultured for obtaining the oxidase. The addition of tryptophan is performed collectively, intermittently or continuously in the range (e.g., 0.1 to 10%) in which the objective reaction is not inhibited. When added, the substrate can be added in the state of an aqueous solution or a slurry. For the purpose of increasing a solubility and facilitating the dispersion, the substrate may be mixed with the organic solvent or the surfactant that has no effect on the reaction.

In the production method of the present invention, reaction conditions can be determined appropriately. A reaction pH is ordinary 3 to 10 and preferably 5 to 9. A reaction temperature is ordinary 10 to 60° C. and preferably 20 to 40° C. A reaction period of time is ordinary 0.5 to 120 hours and preferably 0.5 to 24 hours. If necessary, stirring may be carried out and the cultivation may be stationary cultivation.

Produced 3-indole-pyruvic acid is recovered by the standard method, and can be purified if necessary. When it is necessary to prevent the decomposition of the produced 3-indole-pyruvic acid after the cultivation, a degassing treatment or a deoxidization treatment can also be carried out.

3-Indole-pyruvic acid produced by the production method of the present invention [step (1) in the reaction formula 7] as shown in the following reaction formula 7 is useful as a starting material of 4-(indole-3-ylmethyl)-4-hydroxy-glutamic acid {3-(1-amino-1,3-dicarboxy-3-hydroxy-butane-4-yl)indole} [monatin] that is useful as a sweetener. That is, a precursor keto acid (IHOG) is synthesized by aldol condensation of 3-indole-pyruvic acid and pyruvic acid [step (2) in the reaction formula 7], and IHOG can be aminated at the 2-position in the presence of an enzyme, to synthesize monatin [step (3) in the reaction formula 7].

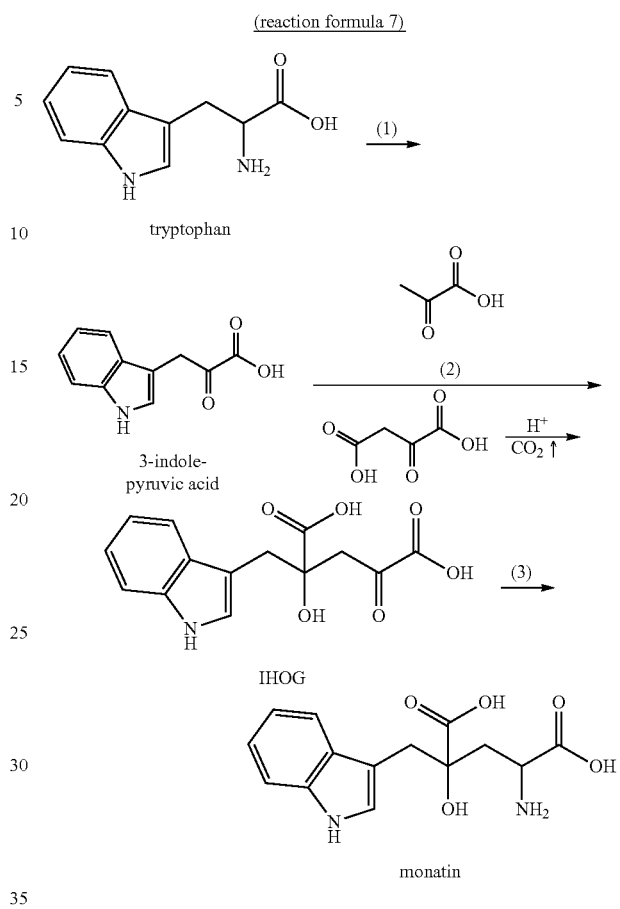

One preferable embodiment of the method for producing 3-indole-pyruvic acid according to the present invention may include the embodiment in which superoxide dismutase (hereinafter sometimes abbreviated as SOD) is added to the reaction system. Produced 3-indole-pyruvic acid can be oxidized spontaneously to generate superoxide depending on the condition. The generated superoxide decomposes 3-indole-pyruvic acid, and the decomposition of 3-indole-pyruvic acid rapidly progresses by a radical reaction in some cases. Thus, by adding SOD in the reaction system, the superoxide is eliminated in the reaction system and the decomposition of 3-indole-pyruvic acid by the superoxide can be inhibited. In addition to SOD, the addition of a radical scavenger such as mercaptoethanol can also prevent the decomposition of 3-indole-pyruvic acid.

It has been speculated that when SOD is used, hydrogen peroxide is generated and 3-indole-pyruvic acid can be decomposed by hydrogen peroxide. However, unexpectedly, by the addition of SOD, the amount of 3-indole-pyruvic acid present in the reaction system could be kept as demonstrated in the following Example. Although its mechanism is not exactly clear, it is speculated that the superoxide has a stronger decomposition action upon 3-indole-pyruvic acid than hydrogen peroxide, thus even when the amount of hydrogen peroxide is slightly increased, by adding SOD in the reaction system to eliminate the superoxide, 3-indole-pyruvic acid can stably remain in the reaction system.

SOD is obtainable as a commercially available enzyme. SOD may be added as the purified enzyme to the reaction system. A transformant that expresses SOD may be made and the transformant or a culture thereof may be added to the reaction system. Nucleotide sequences of genes encoding SOD (sod gene), e.g., sodA gene, sodB gene and sodC gene have been published on public databases. With reference to these databases, a nucleic acid fragment encoding SOD can be amplified and the transformant can be made using this.

When the transformant is made, the transformant transformed so as to express the amino acid oxidase may further be transformed so as to express SOD, or alternatively the respective transformants may be made separately and allowed to coexist in the reaction system. When the amino acid oxidase and SOD are co-expressed in one transformant, the nucleic acid fragments encoding each protein may independently be incorporated into each plasmid, or alternatively both the nucleic acid fragments may tandemly incorporated into one plasmid.

SOD is present as a microbial intracellular enzyme accumulated in the microbial cell in some cases. Thus, one preferable embodiment may include the embodiment in which SOD is allowed to be released from an inside of the transformant. SOD may be released by rupturing the membrane of the transformant. For example, the transformant expressing SOD may be cultured to accumulate a sufficient amount of SOD in the transformant, and the membrane of the transformant may be ruptured to release SOD accumulated in the transformant from the inside of the transformant. By rupturing the membrane of the transformant that supplies SOD, a contact probability of SOD and the superoxide can further be enhanced. As a result, the decomposition of 3-indole-pyruvic acid can be supressed to enhance the yield of 3-indole-pyruvic acid. The rupture of the membrane may be breaking the cell membrane of the transformant. The rupture of the membrane may include sonication and bacterial lysis using a solvent such as toluene, and the like. When the membrane is ruptured using toluene, toluene deactivates the amino acid oxidase in some cases. Thus, SOD is produced separately from the production of the amino acid oxidase and the reaction system using this, and SOD may be isolated and added to the reaction system.

EXAMPLES

Example 1

Microorganism Producing 3-indole-pyruvic acid (IPA)

A medium containing 3 g of ammonium sulfate, 1 g of monopotassium phosphate, 3 g of dipotassium phosphate, 10 mg of iron sulfate, 10 mg of manganese sulfate, 10 g of yeast extract and 10 g of peptone in 1 liter (pH 7.0) was made, 50 mL of the medium was dispensed into a 500 mL Sakaguchi flask, which was then sterilized at 120° C. for 20 minutes to use for the cultivation of microorganisms (medium 1). A slant agar medium (agar 20 g/L) containing 18 g of usual broth in 1 liter was prepared. One loopful of the microorganisms cultured on this slant agar medium at 30° C. for 24 hours was inoculated and cultured with shaking at 30° C. at 120 reciprocations/min for 16 hours. After the cultivation, microbial cells were centrifuged and prepared as the wet microbial cells.

The microorganisms were added into 20 mM Tris-HCl buffer (pH 8.0) containing 10 g/L L-Trp so that a weight of the wet microbial cells was 1% (w/v) in a total amount of 50 mL and then the reaction was performed at 30° C. for one hour. When the wet microbial cells of *Providencia rettgeri* were added, the production of 5.25 g/L 3-indole-pyruvic acid (IPA) was confirmed.

Example 2

Isolation of Amino Acid Oxidase (Deaminase) Enzyme Gene Derived from *Providencia rettgeri*

The isolation of an amino acid oxidase (deaminase) enzyme gene will be described below. *Providencia rettgeri* AJ2770 strain was used as the microorganism. *Escherichia coli* JM109 strain was used as a host for the isolation of the gene, and pUC118 was used as a vector.

*Providencia rettgeri* AJ2770 strain was cultured on the agar medium containing 18 g/L of the usual broth at 30° C. for 24 hours. One loopful of the microbial cells was inoculated in the 500 mL of Sakaguchi flask in which 50 mL of the medium 1 had been placed, and cultured with shaking at 30° C.

The medium (50 mL) after the cultivation was centrifuged (8,000 rpm, 4° C., 10 minutes), and the microorganisms were collected. Chromosomal DNA was acquired from this microbial cells using QIAGEN Genomic-tip System (Qiagen) based on the method of its instructions.

The chromosomal DNA (5 μg) prepared from *Providencia rettgeri* AJ2770 strain was completely digested with BamHI. DNAs (2 kb to 10 kb) were separated on 0.8% agarose gel electrophoresis, purified using Gene Clean II Kit (supplied from Funakoshi Corporation), and dissolved in 10 μL of TE (Tris-EDTA). 4.5 μL of 10 μL TE, pUC118 BamHI and BAP (supplied from Takara Shuzo Co., Ltd.) were mixed and ligated using DNA Ligation Kit Ver. 2 (supplied from Takara Shuzo Co., Ltd.). 0.5 μL of this ligation reaction solution and 100 μL of competent cells of *Escherichia coli* JM109 (supplied from Toyobo Co., Ltd.) were mixed to transform *Escherichia coli*. The resulting transformant was applied on a solid medium appropriate for the cultivation of *E. coli* to prepare a chromosomal DNA library.

A colony formed on a fixed medium was inoculated in TB medium (24 g of yeast extract, 12 g of peptone, 4 mL of glycerol, 1 g of monopotassium phosphate and 3 g of dipotassium phosphate in 1 liter, pH 7.0) in a 96-well plate and cultured at 30° C. overnight. 100 μL of this cultured microbial medium was added to 100 μL of 20 mM Tris-HCl buffer (pH 8.0) containing 10 g/L L-Trp, and reacted with shaking at 30° C. at 120 reciprocations/min. A strain that developed a red color was collected as a bacterial strain having an L-Trp deaminase activity.

Concerning an activity unit (amino acid oxidase activity) of the enzyme used in the present invention, the amount of the enzyme that converted 1 μmole of L-Trp per one minute was defined as one unit (U) when 20 mM Tris-HCl buffer (pH 8.0) containing 10 g/L L-Trp was reacted with shaking at 30° C. at 120 reciprocations/min.

The strain in which the amino acid oxidase (deaminase) activity had been confirmed by the colorimetric method was cultured at 37° C. for 16 hours in a test tube in which 3 mL of the TB medium containing 50 mg/L ampicillin had been placed. The strain had 2.84 U of the amino acid oxidase (deaminase) activity per 1 mL of the medium. Therefore, the cloned gene was confirmed to be expressed in *E. coli*. This strain was designated as pTB2 strain. No activity was detected in the transformant in which pUC118 alone had been introduced as a control.

The plasmid possessed by *Escherichia coli* JM109 was prepared from the above bacterial strain confirmed to have the amino acid oxidase (deaminase) activity using QIAprep Spin Miniprep Kit (250) (supplied from QIAGEN), and a nucleotide sequence of the inserted DNA fragment was determined. A sequencing reaction was carried out using BigDye Terminator v3.1 Cycle Sequencing Kit (supplied from Applied Biosystems) based on its instructions. The electrophoresis was carried out using 3100 genetic analyzer (supplied from Applied Biosystems).

As a result, since an open reading frame encoding the protein having the homology to the amino acid oxidase (deaminase) was present, the cloned gene was confirmed to be the gene encoding the amino acid oxidase (deaminase). The nucleotide sequence of the full length of the amino acid oxidase (deaminase) gene and the amino acid sequence corresponding thereto were shown in SEQ ID NO:1. The homology of the obtained open reading frame was analyzed using BLASTP program. As a result, the homology of 71% to amino acid deaminase derived from *Proteus mirabilis* (gb|AAA86752.1|) and the homology of 57% to amino acid deaminase derived from *Proteus vulgaris* (EC 3.5.4.-) were calculated.

Example 3

Preparation of Ps_aad Expressing Strain

A promoter region of trp operon on the chromosomal DNA of *Escherichia coli* W3110 was amplified by PCR using oligonucleotides shown in SEQ ID NO:3 and SEQ ID NO:4 as the primers. The resulting DNA fragment was ligated to pGEM-Teasy vector (supplied from Promega). *E. coli* JM109 was transformed with this ligation solution, and a strain having an objective plasmid in which the trp promoter had been inserted in a direction opposite to a direction of lac promoter was selected from ampicillin resistant strains. Then, a DNA fragment containing the trp promoter obtained by treating this plasmid with EcoO109I/EcoRI was ligated to pUC19 (supplied from Takara) treated with EcoO109I/EcoRI. *E. coli* JM109 was transformed with this ligation solution, and a strain having an objective plasmid was selected from ampicillin resistant strains. Subsequently, a DNA fragment obtained by treating this plasmid with HindIII/PvuII was ligated to a DNA fragment containing rrnB terminator obtained by treating pKK223-3 (supplied from Amersham Pharmacia) with HindIII/HincII. *E. coli* JM109 was transformed with this ligation solution, and a strain having an objective plasmid was selected from ampicillin resistant strains. The obtained plasmid was designated as pTrp4.

An objective gene was amplified by PCR using the plasmid possessed by the above strain confirmed to have the amino acid oxidase (deaminase) activity as the template and using the oligonucleotides shown in SEQ ID NO:5 and SEQ ID NO:6 as the primers. This DNA fragment was treated with NdeI/HindIII, and the resulting DNA fragment was ligated to pTrp4 treated with NdeI/HindIII. *E. coli* JM109 was transformed with this ligation solution, and a strain having an objective plasmid was selected from ampicillin resistant strains. This plasmid was designated as pTrP4-Ps_aad.

*E. coli* JM109 having pTrP4-Ps_aad was cultured on LB agar medium containing 50 mg/L ampicillin at 37° C. for 16 hours. One loopful of the obtained microbial cells was inoculated into a 500 mL Sakaguchi flask in which 50 mL of the TB medium (containing 50 mg/L ampicillin) had been placed, and a main cultivation was performed at 37° C. for 16 hours. Since 1 mL of the medium showed 0.74 U of the amino acid oxidase (deaminase) activity, the cloned gene was confirmed to be expressed in *E. coli*. No activity was detected in the transformant in which pTrp4 alone had been introduced as the control.

Example 4

Evaluation of L-Trp Oxidization Activity in Parent Strain and Transformant

*Providencia rettgeri* AJ2770 strain was cultured on the agar medium containing 18 g/L of the usual broth at 30° C. for 24 hours. One loopful of this microbial cell was inoculated into a 500 mL Sakaguchi flask in which 50 mL of the medium 1 had been placed, and cultured with shaking at 30° C. for 16 hours. The resulting cultured medium had 0.69 U of an L-Trp oxidization activity per 1 mL of the medium.

One loopful of pTB2 strain was inoculated into a 500 mL Sakaguchi flask in which 50 mL of the TB medium containing 100 mg/L ampicillin had been placed, and cultured with shaking at 37° C. for 16 hours. The resulting cultured medium had 3.5 U of the L-Trp oxidization activity per 1 mL of the medium. It was confirmed that pTB2 strain had the L-Trp oxidization activity that was about 5 times higher than *Providencia rettgeri* AJ2770 strain.

Example 5

Conversion Reaction from Trp to IPA

One loopful of pTB2 strain was inoculated into a 500 mL Sakaguchi flask in which 50 mL of the TB medium containing 100 mg/L ampicillin had been placed, and cultured with shaking at 37° C. for 16 hours. 25 mL of the resulting cultured medium was inoculated into a 5000 mL Sakaguchi flask in which 500 mL of the TB medium containing 100 mg/L ampicillin had been placed, and cultured with shaking at 37° C. for 16 hours. Each reaction solution (300 mL) containing 100 mmol/L of L-Trp, 20 mM Tris-HCl and 0.0025% disfoam GD-113-K (supplied from NOF Corporation) at pH 7.0 was prepared so as to include 120 mL of the resulting cultured medium therein.

The reaction was performed using a 1 liter jar fermenter by stirring at 100, 200, 300 or 400 rpm at 30° C. Air was ventilated at a flow rate of 300 mL/minute. IPA contained in the reaction solution was quantified. A concentration and a reaction time when IPA had achieved the highest concentration were confirmed, and the concentration was 74 mM (after 28 hours) at 100 rpm, 85 mM (after 11 hours) at 200 rpm, 80 mM (after 4 hours) at 300 rpm or 70 mM (after 2 hours) at 400 rpm.

Example 6

Recovery of IPA

One loopful of pTB2 strain was inoculated into a 500 mL Sakaguchi flask in which 50 mL of the TB medium containing 100 mg/L ampicillin had been placed, and cultured with shaking at 37° C. for 16 hours. 25 mL of the resulting cultured medium was inoculated into a 5000 mL Sakaguchi flask in which 500 mL of the TB medium containing 100 mg/L ampicillin had been placed, and cultured with shaking at 37° C. for 16 hours. Each reaction solution (300 mL) containing 100 mmol/L of L-Trp and 0.0025% disfoam GD-113-K at pH 7.0 was prepared so as to include 120 mL of the resulting cultured medium therein.

The reaction was performed using a 500 mL four-necked flask by stirring at 400 rpm at 30° C. The air was ventilated at a flow rate of 300 mL/minute. After reacting for 5.5 hours, the ventilation of the air was stopped, and argon gas was ventilated. Subsequently, the reaction solution was adjusted to pH 4.0 using 1 M sulfuric acid, and centrifuged to remove the microbial cells. 1 M sulfuric acid was added to the resulting supernatant to adjust pH to 2.0. The supernatant was stirred at 20° C. overnight to conduct neutralization crystallization. A crystal was filtrated, washed with water and dried under reduced pressure to yield 3.81 g of IPA crystal with a purity of 90%. As described above, IPA could be recovered by the convenient method without utilizing a complicate purification step using an ion exchange resin and the like.

Example 7

Evaluation of Addition Effect of Superoxide Dismutase (SOD) or Mercaptoethanol as Stabilizing Factor for IPA Each solution (1 mL) containing 10 mM IPA, 10 mM Tris-HCl and 1% acetonitrile was placed in a test tube, and shaken at 25° C. at 150 reciprocations/min for 10 hours. Then, IPA contained in the solution was quantified, and reduced to 2.6 mM.

SOD (1, 10 and 100 U/mL), catalase (100 U/mL), ascorbic acid (10 mL), tocopherol (10 mM), DTT (1 and 10 mM), sodium hydrosulfate (10 mM), mercaptoethanol (1 and 10%), ethanol (10%), methanol (10%), glycerol (10%), SDS (10 mM), Tween 20 (10%), Triton X-100 (10%), sodium borate buffer (10 mM), Tiron (10 mM) or sodium thiosulfate (10 mM) was individually added to the above IPA solution, and shaken likewise. IPA was quantified in each case. Results are shown in Table 1.

TABLE 1

| Additive | Concentration | Residual IPA (mM) |
| --- | --- | --- |
| None | | 2.6 |
| SOD | 1 U/ml | 8.8 |
| SOD | 10 U/ml | 10.5 |
| SOD | 100 U/ml | 10.8 |
| Catalase | 100 U/ml | 4.4 |
| Ascorbic acid | 10 mM | 3.0 |
| Tocopherol | 10 mM | 2.7 |
| DTT | 1 mM | 3.1 |
| DTT | 10 mM | 0.74 |
| Sodium hydrosulfate | 10 mM | 3.2 |
| Mercaptoethanol | 1% | 6.4 |
| Mercaptoethanol | 10% | 9.1 |
| Ethanol | 10% | 2.8 |
| Methanol | 10% | 3.3 |
| Glycerol | 10% | 2.0 |
| SDS | 10 mM | 4.3 |
| Tween 20 | 10% | 3.9 |
| Triton X-100 | 10% | 3.7 |
| sodium borate buffer | 10 mM | 1.5 |
| Triton | 10 mM | 0.50 |
| Sodium thiosulfate | 10 mM | 2.4 |

Example 8

Conversion Reaction from Trp to IPA in the Case of Adding SOD

One loopful of pTB2 strain was inoculated into a 500 mL Sakaguchi flask in which 50 mL of the TB medium containing 100 mg/L ampicillin had been placed, and cultured with shaking at 37° C. for 16 hours. A reaction solution (1 mL) of 150 mmol/L L-Trp and 20 mM Tris-HCl at pH 7.0 was prepared so as to include 0.4 mL of the resulting cultured medium therein. SOD (E. coli-MnSOD, Sigma) was added to the reaction solution at a final concentration of 100 U/mL.

Each reaction solution (1 mL) was placed in a test tube, and shaken at 25° C. at 150 reciprocations/min for 6 hours. The amount of IPA produced in the reaction solutions was 61 mM in the absence of SOD and 120 mM in the presence of SOD.

Example 9

Construction of SOD-expressing Strain

E. coli JM109 strain was cultured on the LB agar medium at 37° C. for 16 hours. A DNA fragment containing a sodA gene was amplified by PCR using this microbial cells as the template. The sodA gene encodes SOD A (Mn type) and its sequence had been registered as accession number of EG10953 on the public database such as ecogene (URL: http://ecogene.org/index.php). SD-Nde-sodA-f (SEQ ID NO:7) and sodA-Hind-r (SEQ ID NO:8) were used as the primers. The resulting DNA fragment was digested with NdeI and HindIII, and ligated to the vector pSFN described in International Publication No. 2006/075486 Pamphlet (pSFN Sm_Aet in Examples, particularly see Examples 1, 6 and 12), which was digested with NdeI and HindIII similarly. E. coli JM109 strain was transformed with this ligation solution and a strain having an objective plasmid was selected from ampicillin resistant strains. The obtained plasmid was designated as pSFN-sodA.

Likewise, pSFN-sodB [SD-Nde-sodB-f (SEQ ID NO:9) and sodB-Hind-r (SEQ ID NO:10) were used as the primers] and pSFN-sodC [SD-Nde-sodC-f (SEQ ID NO:11) and sodC-Hind-r (SEQ ID NO:12) were used as the primers] were constructed. pSFN-sodB is the plasmid in which a DNA fragment containing a sodB gene has been incorporated. pSFN-sodC is the plasmid in which a DNA fragment containing a sodC gene has been incorporated. SOD A (Mn type) that is an expression product of the sodA gene, SOD B (Fe type) that is an expression product of the sodB gene and SOD C (Cu—Zn type) are isozymes. The sequences of the sodB gene and the sodC gene had been registered as the accession numbers EG10954 and EG13419, respectively on the public database such as ecogene.

pSFN vector digested with NdeI and HindIII was ligated to a DNA fragment having multicloning sites, which was obtained by digesting pTrp4 with NdeI and HindIII. E. coli JM109 strain was transformed with this ligation solution and a strain having an objective plasmid was selected from ampicillin resistant strains. The obtained plasmid was designated as pSFN-mcs.

Example 10

Measurement of SOD Activity of SOD-expressing Strains

The constructed SOD-expressing plasmid, pSFN-sodA was introduced into E. coli JM109 strain, and one loopful of the transformant was inoculated into 50 mL of the TB medium containing 100 mg/L ampicillin, and cultured with shaking at 37° C. for 16 hours to obtain a cultured medium.

Likewise, a cultured medium of a transformant carrying pSFN-sodB, a cultured medium of a transformant carrying pSFN-sodC and a cultured medium of a transformant carrying pSFN-mcs were obtained.

Microbial cells were collected from these cultured media, and suspended in BugBuster master mix (Novagen) to prepare microbial cell extract solutions. The SOD activity in the obtained microbial cell extract solution was measured using SOD Assay Kit-WST (Dojindo) and the SOD activity per 1 mL of the cultured medium was calculated. SOD (*E. coli*-MnSOD, Sigma) was used as the standard. 0.01 mM CuCl$_2$ was added to the microbial cell extract solution of the SOD C-expressing strain, and the SOD activity was measured.

As a result, it was demonstrated that any of the SOD-expressing strains had the higher SOD activity than pSFN-mcs strain. The results are shown in Table 2.

TABLE 2

| Plasmid | SOD activity (U/ml) |
| --- | --- |
| pSFN-mcs | 53 |
| pSFN-sodA | 189 |
| pSFN-sodB | 874 |
| pSFN-sodC | 7700 |

Example 11

Conversion Reaction from Trp to IPA Using SOD-expressing Strain

A reaction solution (1 mL) of 200 mmol/L L-Trp and 20 mM Tris-HCl at pH 7.0 was prepared so as to include 0.1 mL of the cultured medium of the SOD-expressing strain and 0.4 mL of the cultured medium of pTB2 strain. Toluene (1%) was added to the cultured medium of the SOD A-expressing strain, which was mixed and stirred, and then added to the reaction solution. Likewise, toluene (1%) was mixed and stirred with the cultured medium of the SOD B-expressing strain, which was then added to the reaction solution. CuCl$_2$ was added to the cultured medium of the SOD C-expressing strain at the final concentration of 0.01 mM and they were stirred, which was then added to the reaction solution. A reaction solution containing no cultured medium of the SOD-expressing strain, and a reaction solution in which SOD (*E. coli*-MnSOD, Sigma) had been added at final concentration of 100 U/mL were also prepared.

Each reaction solution (1 mL) was shaken at 25° C. at 140 reciprocations/min for 6 hours using the test tube. IPA contained in the resulting reaction solution was quantified, and the highest concentration of IPA that was 129 mM was confirmed when the cultured medium of the SOD B-expressing strain treated with toluene had been added. The results are shown in Table 3.

TABLE 3

| Additive | IPA (mM) |
| --- | --- |
| — | 96 |
| SOD (sigma) | 123 |
| Cultured medium of SodA-expressing strain | 100 |
| Cultured medium of SodA-expressing strain + Toluene | 109 |
| Cultured medium of SodB-expressing strain | 119 |
| Cultured medium of SodB-expressing strain + Toluene | 129 |
| Cultured medium of SodC-expressing strain | 98 |
| Cultured medium of SodC-expressing strain + CuCl$_2$ | 123 |

---

What we claim is:

1. A method for producing 3-indole-pyruvic acid, comprising converting tryptophan into 3-indole-pyruvic acid in the presence of an isolated recombinant host cell and/or a culture thereof,
wherein the recombinant host cell comprises a recombinant polynucleotide comprising a polynucleotide selected from the group consisting of the following (a) to (d):
(a) a polynucleotide encoding a protein comprising the amino acid sequence of SEQ ID NO:2;
(b) a polynucleotide encoding a protein which consists of an amino acid sequence comprising a substitution, deletion and/or insertion of one to ten amino acids in the amino acid sequence of SEQ ID NO:2 and has an L-Trp deaminase activity;
(c) a polynucleotide encoding a protein which consists of an amino acid sequence having 95% or more homology to the amino acid sequence of SEQ ID NO:2 and has an L-Trp deaminase activity; and
(d) a polynucleotide comprising the nucleotide sequence of nucleotide positions 61 to 1476 in the nucleotide sequence of SEQ ID NO:1.

2. The method for producing 3-indole-pyruvic acid according to claim 1, wherein the polynucleotide is (a) a polynucleotide encoding a protein comprising the amino acid sequence of SEQ ID NO:2.

3. The method for producing 3-indole-pyruvic acid according to claim 1, wherein the polynucleotide is (d) a polynucleotide comprising the nucleotide sequence of nucleotide positions 61 to 1476 in the nucleotide sequence of SEQ ID NO:1.

4. The method for producing 3-indole-pyruvic acid according to claim 1, further comprising adding a superoxide dismutase to a reaction system which converts the tryptophan into the 3-indole-pyruvic acid.

5. The method for producing 3-indole-pyruvic acid according to claim 1, further comprising adding a recombinant host cell which expresses superoxide dismutase and/or a culture thereof to a reaction system which converts the tryptophan into the 3-indole-pyruvic acid.

6. The method for producing 3-indole-pyruvic acid according to claim 5, further comprising obtaining said culture by rupturing cell membrane of the host cell.

7. A method for producing 3-indole-pyruvic acid, comprising converting tryptophan into 3-indole-pyruvic acid in the presence of an isolated recombinant host cell and/or a culture thereof,
wherein the recombinant host cell comprises a recombinant polynucleotide comprising a polynucleotide encoding a protein which consists of an amino acid sequence comprising a substitution, deletion and/or insertion of one to ten amino acids in the amino acid sequence of SEQ ID NO:2 and has an L-Trp deaminase activity.

8. The method for producing 3-indole-pyruvic acid according to claim 7, further comprising adding a superoxide dismutase to a reaction system which converts the tryptophan into the 3-indole-pyruvic acid.

9. The method for producing 3-indole-pyruvic acid according to claim 7, further comprising adding a recombinant host cell which expresses superoxide dismutase and/or a culture thereof to a reaction system which converts the tryptophan into the 3-indole-pyruvic acid.

10. The method for producing 3-indole-pyruvic acid according to claim 9, further comprising obtaining said culture by rupturing cell membrane of the host cell.

11. A method for producing 3-indole-pyruvic acid, comprising converting tryptophan into 3-indole-pyruvic acid in the presence of an isolated recombinant host cell and/or a culture thereof,
wherein the recombinant host cell comprises a recombinant polynucleotide comprising a polynucleotide encoding a protein which consists of an amino acid sequence having 95% or more homology to the amino acid sequence of SEQ ID NO:2 and has an L-Trp deaminase activity.

12. The method for producing 3-indole-pyruvic acid according to claim 11, further comprising adding a superoxide dismutase to a reaction system which converts the tryptophan into the 3-indole-pyruvic acid.

13. The method for producing 3-indole-pyruvic acid according to claim 11, further comprising adding a recombinant host cell which expresses superoxide dismutase and/or a culture thereof to a reaction system which converts the tryptophan into the 3-indole-pyruvic acid.

* * * * *

UNITED STATES PATENT AND TRADEMARK OFFICE
CERTIFICATE OF CORRECTION

PATENT NO.        : 8,518,665 B2                    Page 1 of 1
APPLICATION NO.   : 13/684888
DATED             : August 27, 2013
INVENTOR(S)       : Yasuaki Takakura et al.

It is certified that error appears in the above-identified patent and that said Letters Patent is hereby corrected as shown below:

On the title page, Item 71, should read:

-- (71) Ajinomoto Co., Inc., Tokyo (JP) --

Signed and Sealed this
Fourteenth Day of April, 2015

Michelle K. Lee
*Director of the United States Patent and Trademark Office*

SEQUENCE LISTING

```
<160> NUMBER OF SEQ ID NOS: 12

<210> SEQ ID NO 1
<211> LENGTH: 1600
<212> TYPE: DNA
<213> ORGANISM: Providencia rettgeri
<220> FEATURE:
<221> NAME/KEY: CDS
<222> LOCATION: (61)..(1476)

<400> SEQUENCE: 1
cataatctca atttgaaatt atttactata taaaaaacaa gattgttatt gaggttatag      60 atg aaa atc tcg aga aga aag cta tta tta ggg gtt ggt gct gct ggt     108
Met Lys Ile Ser Arg Arg Lys Leu Leu Leu Gly Val Gly Ala Ala Gly
1               5                  10                  15 gtt tta gca ggg ggt gct gcg gtt gtt cct atg atc aat cgt gaa ggt     156
Val Leu Ala Gly Gly Ala Ala Val Val Pro Met Ile Asn Arg Glu Gly
                20                  25                  30 cgt ttt gaa tcg act aaa tca cgt gta cca gct gtt gct ggc aca gaa     204
Arg Phe Glu Ser Thr Lys Ser Arg Val Pro Ala Val Ala Gly Thr Glu
            35                  40                  45 ggc aaa tta cca gag tct gca gat gca gtc atc atc ggt gcc ggc ctt     252
Gly Lys Leu Pro Glu Ser Ala Asp Ala Val Ile Ile Gly Ala Gly Leu
        50                  55                  60 caa ggg atc atg act gca att aac ctt gct gaa aaa ggt ctt aat gtt     300
Gln Gly Ile Met Thr Ala Ile Asn Leu Ala Glu Lys Gly Leu Asn Val
65                  70                  75                  80 gtt atc tgt gaa aaa ggt gtt gtc ggt ggt gag caa tca ggc cgt gca     348
Val Ile Cys Glu Lys Gly Val Val Gly Gly Glu Gln Ser Gly Arg Ala
                85                  90                  95 tat agc caa att atc agt tat aag act tcc cca gct att ttc cct tta     396
Tyr Ser Gln Ile Ile Ser Tyr Lys Thr Ser Pro Ala Ile Phe Pro Leu
```

-continued

```
                   100                 105                 110
cac cat tac gga aaa att caa tgg ctt ggc atg aac gaa aaa atc ggt    444
His His Tyr Gly Lys Ile Gln Trp Leu Gly Met Asn Glu Lys Ile Gly
            115                 120                 125 gct gat acc agc tac cgt gtt caa ggc cgt gtt gaa gta cct tca agc    492
Ala Asp Thr Ser Tyr Arg Val Gln Gly Arg Val Glu Val Pro Ser Ser
130                 135                 140 gaa gaa gat tta gaa att tca aga gcc tgg att aaa tct gca tct gaa    540
Glu Glu Asp Leu Glu Ile Ser Arg Ala Trp Ile Lys Ser Ala Ser Glu
145                 150                 155                 160 aac cca ggt ttc gat aca cct tta cgt acc cgt atg att gaa gga act    588
Asn Pro Gly Phe Asp Thr Pro Leu Arg Thr Arg Met Ile Glu Gly Thr
                165                 170                 175 gaa ctg gcg aat cgt ctg gtt gat gca caa act cca tgg aaa atc ggt    636
Glu Leu Ala Asn Arg Leu Val Asp Ala Gln Thr Pro Trp Lys Ile Gly
            180                 185                 190 gga ttt gaa gaa gac tca ggt agc ctt gac cct gaa gtt gtc aca cca    684
Gly Phe Glu Glu Asp Ser Gly Ser Leu Asp Pro Glu Val Val Thr Pro
        195                 200                 205 acc atg gca aac tac gca aaa tca atc ggt att cgc atc tac acc aat    732
Thr Met Ala Asn Tyr Ala Lys Ser Ile Gly Ile Arg Ile Tyr Thr Asn
210                 215                 220 tgc gca gta cgt ggt att gaa acg gcg ggc ggc aaa att tct gat gtt    780
Cys Ala Val Arg Gly Ile Glu Thr Ala Gly Gly Lys Ile Ser Asp Val
225                 230                 235                 240 gtc aca gaa aaa ggt gca atc aaa act tct cgt gtt gtt ctg acg ggc    828
Val Thr Glu Lys Gly Ala Ile Lys Thr Ser Arg Val Val Leu Thr Gly
                245                 250                 255 ggt att tgg tcg cgt ctg ttc atg ggt aac tta ggc att gat gtt cca    876
Gly Ile Trp Ser Arg Leu Phe Met Gly Asn Leu Gly Ile Asp Val Pro
            260                 265                 270 aca ctg aac gtt tac cta tca caa cag cgt att act ggc gta cca ggc    924
Thr Leu Asn Val Tyr Leu Ser Gln Gln Arg Ile Thr Gly Val Pro Gly
        275                 280                 285 gca cca aaa ggt aac gtc cac tta cct aac ggt att cac ttc cgt gaa    972
Ala Pro Lys Gly Asn Val His Leu Pro Asn Gly Ile His Phe Arg Glu
290                 295                 300 caa gct gat ggt acc tac gcc gtt gcg cca cgt atc ttt act agc tct   1020
Gln Ala Asp Gly Thr Tyr Ala Val Ala Pro Arg Ile Phe Thr Ser Ser
305                 310                 315                 320 atc gta aaa gac agc ttc ctg tta gga cca aga ttc cta cac gta tta   1068
Ile Val Lys Asp Ser Phe Leu Leu Gly Pro Arg Phe Leu His Val Leu
                325                 330                 335 ggc ggc ggg gaa tta cca tta gag ttc tct ctt ggt aaa gat tta ttc   1116
Gly Gly Gly Glu Leu Pro Leu Glu Phe Ser Leu Gly Lys Asp Leu Phe
            340                 345                 350 aac tcc ttc atg atg gca acg tct tgg aac tta gac gag aaa aca cct   1164
Asn Ser Phe Met Met Ala Thr Ser Trp Asn Leu Asp Glu Lys Thr Pro
        355                 360                 365 ttt gaa gag ttc cgt acc gca act aat aca cca aac aac gaa cac tta   1212
Phe Glu Glu Phe Arg Thr Ala Thr Asn Thr Pro Asn Asn Glu His Leu
370                 375                 380 gat ggc gtt ctg gaa aga ctg aga aaa gaa ttc cca gta ttt aaa gag   1260
Asp Gly Val Leu Glu Arg Leu Arg Lys Glu Phe Pro Val Phe Lys Glu
385                 390                 395                 400 tct aaa gtg gtt gaa cgt tgg ggt ggt acc gtt gca cca acg gat gat   1308
Ser Lys Val Val Glu Arg Trp Gly Gly Thr Val Ala Pro Thr Asp Asp
                405                 410                 415 gaa att cca att att tca aca atc gag cag tat cca gga cta gtc atc   1356
Glu Ile Pro Ile Ile Ser Thr Ile Glu Gln Tyr Pro Gly Leu Val Ile
```

```
                             420                 425                 430
aac acc gcc aca ggc tgg ggt atg acg gaa agc cct gca tct ggt cga     1404
Asn Thr Ala Thr Gly Trp Gly Met Thr Glu Ser Pro Ala Ser Gly Arg
            435                 440                 445 tta acg gca gaa ttg tta atg ggc gaa aca cca ttt att gat cct acg     1452
Leu Thr Ala Glu Leu Leu Met Gly Glu Thr Pro Phe Ile Asp Pro Thr
450                 455                 460 ccg tat aaa ctt tcc cgt ttt agc taaaaacag gaaaaaagc gatttttact     1506
Pro Tyr Lys Leu Ser Arg Phe Ser
465                 470 gtggatctat tagcgaatag tttaaagtta catgaaagtt taatttttga taaaactaat  1566
agatcctatt tactttgata atgttaagga gttt                              1600

<210> SEQ ID NO 2
<211> LENGTH: 472
<212> TYPE: PRT
<213> ORGANISM: Providencia rettgeri

<400> SEQUENCE: 2

Met Lys Ile Ser Arg Arg Lys Leu Leu Leu Gly Val Gly Ala Ala Gly
1               5                   10                  15

Val Leu Ala Gly Gly Ala Ala Val Val Pro Met Ile Asn Arg Glu Gly
            20                  25                  30

Arg Phe Glu Ser Thr Lys Ser Arg Val Pro Ala Val Ala Gly Thr Glu
        35                  40                  45

Gly Lys Leu Pro Glu Ser Ala Asp Ala Val Ile Ile Gly Ala Gly Leu
    50                  55                  60

Gln Gly Ile Met Thr Ala Ile Asn Leu Ala Glu Lys Gly Leu Asn Val
65                  70                  75                  80

Val Ile Cys Glu Lys Gly Val Val Gly Gly Glu Gln Ser Gly Arg Ala
                85                  90                  95

Tyr Ser Gln Ile Ile Ser Tyr Lys Thr Ser Pro Ala Ile Phe Pro Leu
            100                 105                 110

His His Tyr Gly Lys Ile Gln Trp Leu Gly Met Asn Glu Lys Ile Gly
        115                 120                 125

Ala Asp Thr Ser Tyr Arg Val Gln Gly Arg Val Glu Val Pro Ser Ser
    130                 135                 140

Glu Glu Asp Leu Glu Ile Ser Arg Ala Trp Ile Lys Ser Ala Ser Glu
145                 150                 155                 160

Asn Pro Gly Phe Asp Thr Pro Leu Arg Thr Arg Met Ile Glu Gly Thr
                165                 170                 175

Glu Leu Ala Asn Arg Leu Val Asp Ala Gln Thr Pro Trp Lys Ile Gly
            180                 185                 190

Gly Phe Glu Glu Asp Ser Gly Ser Leu Asp Pro Glu Val Val Thr Pro
        195                 200                 205

Thr Met Ala Asn Tyr Ala Lys Ser Ile Gly Ile Arg Ile Tyr Thr Asn
    210                 215                 220

Cys Ala Val Arg Gly Ile Glu Thr Ala Gly Gly Lys Ile Ser Asp Val
225                 230                 235                 240

Val Thr Glu Lys Gly Ala Ile Lys Thr Ser Arg Val Val Leu Thr Gly
                245                 250                 255

Gly Ile Trp Ser Arg Leu Phe Met Gly Asn Leu Gly Ile Asp Val Pro
            260                 265                 270

Thr Leu Asn Val Tyr Leu Ser Gln Gln Arg Ile Thr Gly Val Pro Gly
        275                 280                 285
```

Ala Pro Lys Gly Asn Val His Leu Pro Asn Gly Ile His Phe Arg Glu
        290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Arg Phe Leu His Val Leu
                325                 330                 335

Gly Gly Gly Glu Leu Pro Leu Glu Phe Ser Leu Gly Lys Asp Leu Phe
            340                 345                 350

Asn Ser Phe Met Met Ala Thr Ser Trp Asn Leu Asp Glu Lys Thr Pro
        355                 360                 365

Phe Glu Glu Phe Arg Thr Ala Thr Asn Thr Pro Asn Asn Glu His Leu
370                 375                 380

Asp Gly Val Leu Glu Arg Leu Arg Lys Glu Phe Pro Val Phe Lys Glu
385                 390                 395                 400

Ser Lys Val Val Glu Arg Trp Gly Gly Thr Val Ala Pro Thr Asp Asp
                405                 410                 415

Glu Ile Pro Ile Ile Ser Thr Ile Glu Gln Tyr Pro Gly Leu Val Ile
            420                 425                 430

Asn Thr Ala Thr Gly Trp Gly Met Thr Glu Ser Pro Ala Ser Gly Arg
        435                 440                 445

Leu Thr Ala Glu Leu Leu Met Gly Glu Thr Pro Phe Ile Asp Pro Thr
450                 455                 460

Pro Tyr Lys Leu Ser Arg Phe Ser
465                 470

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtatcacgag gccctagctg tggtgtcatg gtcggtgatc                              40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcggggatt ccatatgata ccctttttac gtgaacttgc                              40

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggaattcca tatgctaccc atacttaata at                                      32

<210> SEQ ID NO 6
<211> LENGTH: 33
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 6
cccaagcttt tagctaaaac gggaaagttt ata                                33

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tataacaccg taaggaggaa tgcatatgag ctatacccctg ccatccctgc              50

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcccaagct tattttttcg ccgcaaaacg tgcc                               34

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aacaccgtaa ggaggaatgc atatgtcatt cgaattacct gcactaccgt atgc         54

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agcccaagct tatgcagcga gattttttcgc tacg                              34

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tataacaccg taaggaggaa tgcatatgaa acgttttagt ctggctattc              50
```

```
<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agcccaagct tacttaatta caccacaggc atag                                34
```